United States Patent [19]

Shinohara et al.

[11] 4,217,345
[45] Aug. 12, 1980

[54] 3-O-(β-D-GLUCURONOPYRANOSYL)-SOYASAPOGENOL B

[75] Inventors: Masanao Shinohara, Naruto; Yoshimasa Nakano, Tokushima; Hirotsugu Kaise, Tokushima; Taketoshi Izawa, Tokushima; Wasei Miyazaki, Tokushima, all of Japan

[73] Assignee: Otsuka Pharmaceutical Co., Ltd., Tokyo, Japan

[21] Appl. No.: 25,518

[22] Filed: Mar. 30, 1979

[30] Foreign Application Priority Data

Mar. 31, 1978 [JP] Japan .................................. 53-38536

[51] Int. Cl.$^2$ ...................... A61K 31/70; C07H 15/24; C07H 15/20
[52] U.S. Cl. ....................................... 424/180; 536/4; 424/182
[58] Field of Search ................... 536/4; 424/180, 181, 424/182

[56] References Cited

PUBLICATIONS

Kitagawa, I., et al., "Chem. Abst.", vol. 84, 1976, 132654k.
Kitagawa, I., et al., "Chem. Abst.", vol. 82, 1975, 98331z.

Primary Examiner—Johnnie R. Brown
Assistant Examiner—Blondel Hazel
Attorney, Agent, or Firm—Sughrue, Rothwell, Mion, Zinn & Macpeak

[57] ABSTRACT

3-O-(β-D-Glucuronopyranosyl)-soyasapogenol B represented by the formula (I):

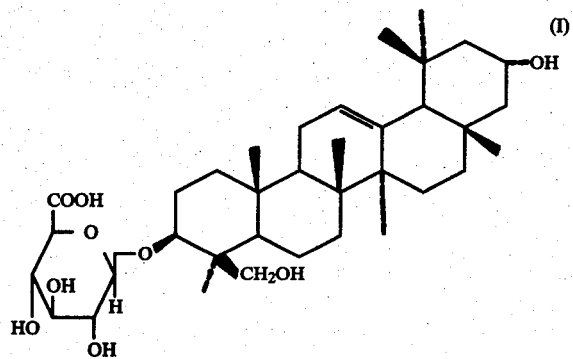

and salts thereof and process for preparing the same are disclosed. The compound represented by the formula (I) and salts thereof have anticomplementary activity and are useful as therapeutic agents for autoimmune diseases, collagen diseases, and rheumatic diseases.

5 Claims, 1 Drawing Figure

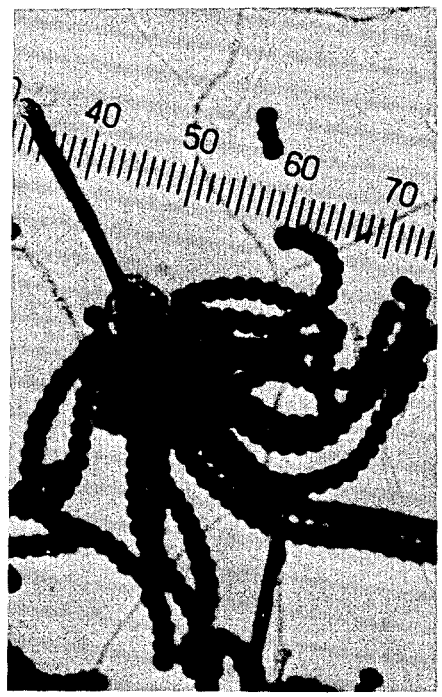

3-O-(β-D-GLUCURONOPYRANOSYL)-SOYASAPOGENOL B

BACKGROUND OF THE INVENTION

1. Field of the Invention

This invention relates to a new compound, 3-O-(β-D-glucuronopyranosyl)-soyasapogenol B, and salts thereof as well as to a process for preparing the same.

The compounds of this invention have anticomplementary activity and are useful as therapeutic agents for autoimmune diseases, collagen diseases, and rheumatic diseases.

2. Description of the Prior Art

Various compounds related to the compound of this invention are known. For example, glycyrrhizin (Yasuhiro Ariga, Hiroyuki Sumi, Yumiko Takada and Akikazu Takada, *Abridgements of Lecture Programs on Seminar of the Plasmin Research Association*, page 65 (1977); Koretsugu Arimoto, Kaneyuki Mineta, Hiroyuki Sumi, Yumiko Takada and Akikazu Takada, *Proceedings of the 14th Symposium on Complements*, p. 79–82 (1977)); and 3-O-(6-O-methyl-β-D-glucuronopyranosyl)-soyasapogenol B (Isao Kitagawa, Masayuki Yoshikawa and Ichiro Yoshioka, *Chem. Pharm. Bull.*, 22, p. 1339 (1974); Ibid., 24, p. 121 (1976)), etc., are known. The former compound has a steroid like structure and exhibits an activity similar to that of steroids. For example, it shows an inhibitory activity against plasmin, urokinase, Kallikrein, thrombin and complements. On the other hand, the physiological activities of the latter have not yet been reported. In contrast, the compound of this invention and salts thereof have an anticomplementary activity which is unexpectedly superior to that of glycyrrhizin and which is quite unexpected from 3-O-(6-O-methyl-β-D-glucuronopyranosyl)-soyasapogenol B as will be apparent from the results of pharmacological tests described hereinafter.

SUMMARY OF THE INVENTION

An object of this invention is to provide a novel soyasapogenol derivative and salts thereof which have anticomplementary activity.

Another object of this invention is to provide a process for preparing a soyasapogenol derivative and salts thereof which have a high anticomplementary activity.

Still another object of this invention is to provide pharmaceutical compositions comprising a soyasapogenol derivative of the formula (I) or salts thereof.

Still another object of this invention is to provide a process for treating nephritis using such a soyasapogenol derivative or salts thereof.

This invention provides a novel soyasapogenol derivative expressed by the following formula (I):

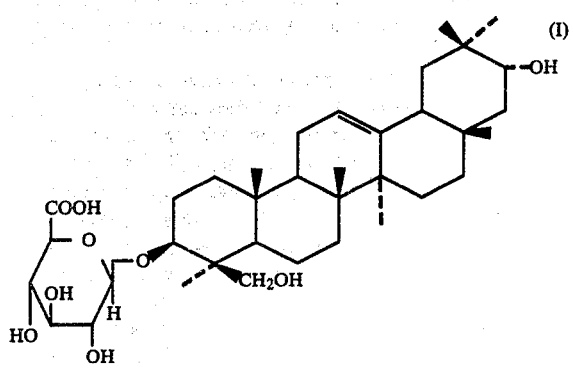

This invention also provides pharmaceutically acceptable salts of the soyasapogenol derivative of the formula (I) above which are obtained by reacting the soyasapogenol derivative with appropriate basic compounds.

This invention also provides processes for the production of the soyasapogenol derivative of the formula (I) above as described in detail hereinafter.

This invention also provides pharmaceutical compositions containing a therapeutically effective amount of the soyasapogenol derivative of the formula (I) above or pharmaceutically acceptable salts thereof for achieving anticomplementary activity in animals and a method of use, particularly treating nephritic disorders in animals, comprising administering the pharmaceutical composition to a patient afflicted with such a disorder.

BRIEF DESCRIPTION OF THE DRAWING

The FIGURE is a microphotograph of Stachybotrys sp. T-791.

DETAILED DESCRIPTION OF THE INVENTION

The compounds of the present invention may be used to relieve or prevent pathological reactions requiring the function of a complement and in the therapeutic treatment of immunologic diseases such as rheumatoid arthritis, systemic lupus erythematosus, glomerulonephritis, autoallergic hemolytic anemia, platelet disorders, vasculitis, etc. The compound of this invention may also be used in the therapeutic treatment of non-immunologic diseases such as paroxyamal nocturnal hemoglobinuria, hereditary angioneurotic edema and inflammatory states induced by the action of bacterial or lysosomal enzymes on the appropriate complement components as, for example, inflammation following coronary occlusion. They may also be useful in the treatment of transplant rejections and as blood culture and transport mediums.

In recent years extensive research has been made on the theoretical analysis of the complement system and its effects on humans and animals and at present it is generally recognized that when certain compounds have an anticomplementary activity they can exhibit therapeutic effects on various symptoms described above. For example, U.S. Pat. No. 4,021,544 discloses the following.

"The term 'complement' refers to a complex group of proteins in body fluids that, working together with antibodies or other factors, play an important role as mediators of immune, allergic, immunochemical and/or immunopathological reactions. The reactions in which a complement participates take place in blood serum or in other body fluids, and hence are considered to be humoral reactions."

"With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 935-938 (1968), *Scientific American*, 229, (No. 5), 54-66 (1973), *Medical World News*, Oct. 11, 1974, pp. 53-58, 64-66, *Harvey Lectures*, 66, 75-104 (1972), *The New England Journal of Medicine*, 287, 489-495, 545-549, 592-596, 642-646 (1972), *The John Hopkins Med. J.*, 128, 57-74 (1971), and *Federation Proceeding*, 32, 134-137 (1973)."

"The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and, (3) an attack unit (C5, C6, C7, C8 and C9) which creates a hole in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword."

"Activation of the complement system also accelerates blood clotting. This action comes about by way of the complement-mediated release of a clotting factor from platelets. The biologically active complement fragment and complexes can become involved in reactions that damage the host's cells, and these pathogenic reactions can result in the development of immune-complex diseases. For example, in some forms of nephritis the complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune-complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes."

"In the presence of antibody-antigen complexes the complement proteins are involved in a series of reactions which may lead to irreversible membrane damage if they occur in the vicinity of biological membranes. Thus, while the complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review in Biochemistry*, 38, 389 (1969)."

"It has been reported that the known complement inhibitors, epsilon-aminocaproic acid, Suramin Sodium and tranexamic acid, have been used with success in the treatment of hereditary angioneurotic edema, a disease state resulting from an inherited deficiency or lack of function of the serum inhibitor of the activated first component of the complement (C1 inhibitor), *The New England Journal of Medicine*, 286, 808-812 (1972); *Allergol; Et. Immunipath;* II, 163-168 (1974); *J. Allergy Clin. Immunol*, 53, No. 5, 298-302 (1974); and *Annals of Internal Medicine*, 84, 580-593 (1976)."

3-O-(β-D-glucuronopyranosyl)-soyasapogenol B obtained according to this invention shows potent anticomplementary activity. Therefore, the compound of this invention is expected to inhibit excessive activation of complement in such diseases as termed "immune-complex diseases" or "autoimmune diseases", for example, nephritis, rheumatic diseases, systemic lupus erythematosus, etc., and to be effective for prophylaxis and the therapy of such diseases.

The compounds of this invention can be prepared in various manners.

For example, the compound of this invention represented by the formula (I) can be isolated and purified with ease by subjecting known saponin-containing plant material such as soybean which contains compounds having a 3-O-(β-D-glucuronopyranosyl)-soyasapogenol moiety as a partial structure to chemical treatments optionally together with physical treatments. For example, the compound represented by the formula (I) can be prepared by first separating soyasaponin B from soybeans and then treating this compound in accordance with Reaction Scheme 1 described hereinafter.

The separation of soyasaponin B can be carried out using known separating processes and means. Examples of suitable chemical treatments include hydrolysis, alcoholysis, etherification, acylation, etc. Examples of suitable physical treatments include solvent extraction, solvent dilution, liquid chromatography, gas chromatography, recrystallization, etc.

More specifically, the compound represented by the formula (I) can be prepared by subjecting soyasaponin B (II) obtained in accordance with the process of Kitagawa et al (Isao Kitagawa, Masayuki Yoshikawa and Ichiro Yoshioka, *Chem. Pharm. Bull.*, 22, p. 1339 (1974), Ibid., 24, p. 121 (1976)) to alcoholysis with a lower alcohol such as methanol, ethanol, propanol, isopropanol, butanol, pentanol, hexanol, etc., in the presence of an acid to form 3-O-(6-O-alkyl-β-D-glucuronopyranosyl)-soyasapogenol B (formula (III)) and then hydrolyzing it (Reaction Scheme-1).

The term "soyasaponin B" as used herein refers to a mixture of soyasaponins I, II and III which contain soyasapogenol B as an aglycon as described in the above-described literature references.

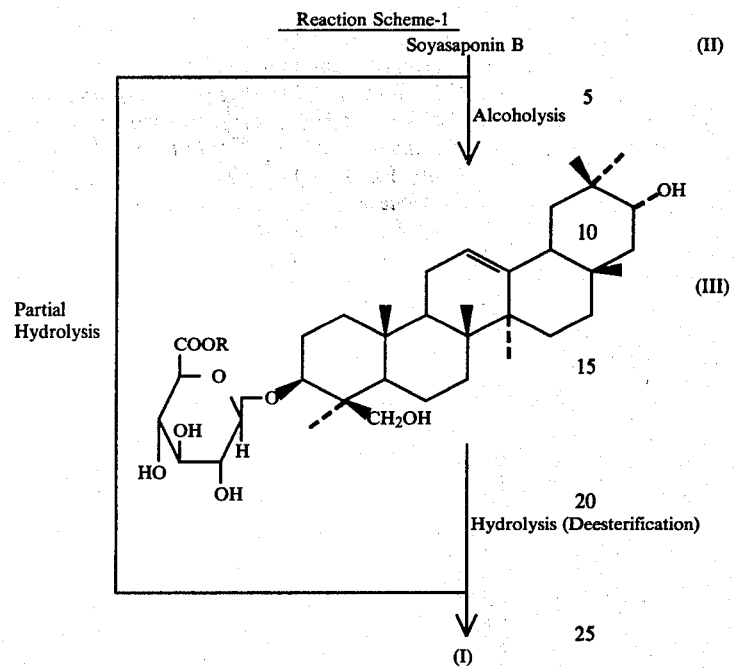

Reaction Scheme-1

In the above formula (III), R represents a lower alkyl group having 1 to 6 carbon atoms.

Various acids conventionally used in alcoholysis can be used in the alcoholysis of soyasaponin B (II) Suitable examples of such acids include hydrogen halides such as hydrogen chloride, hydrogen bromide, etc., strong inorganic acids such as sulfuric acid, nitric acid, etc., strong organic acids such as trichloroacetic acid, trifluoroacetic acid, etc., Lewis acids such as aluminum chloride, boron trifluoride, titanium tetrachloride, titanium tetrabromide, etc.

The alcoholysis can preferably be conducted at room temperature to 150° C., more preferably about 50° to 100° C., for about 1 to about 6 hours.

The method of isolating the compounds represented by the formula (III) from the reaction mixture is not particularly limited and various known methods utilizing the physico-chemical properties of the substances produced including those employed in separating soyasaponin B can be employed. Suitable examples of such methods include a method utilizing the differences in solubility between the products and impurities, a method utilizing the differences in adsorptive power and affinity for ordinary adsorbents such as activated carbon, XAD-2, silica gel, ion exchange resins, Sephadex, etc., a method utilizing the differences in the coefficient of distribution between two liquid phases, and a combination of such methods. For example, the alcoholysate is mixed with water to form precipitates which are subjected to silica gel chromatography and eluted stepwise with an eluant, e.g., a mixture of chloroform and ethanol to isolate the compound of the formula (I).

The hydrolysis of the compound represented by the formula (III) can usually be carried out in an inert solvent in the presence of a catalyst under conditions employed conventionally in the hydrolysis of esters. Conventional catalysts can be used in this reaction. Suitable examples of catalysts which can be used include mineral acids such as hydrochloric acid, sulfuric acid, nitric acid, etc., inorganic basic compounds such as sodium hydroxide, potassium hydroxide, sodium carbonate, sodium hydrogen carbonate, potassium carbonate, potassium hydrogen carbonate, etc. Inorganic basic compounds are preferred as the catalyst.

Any conventional inert solvents can be used in the above reaction. Suitable examples of inert solvents include water, lower alcohols such as methanol, ethanol, propanol, etc., ethers such as dioxane, tetrahydrofuran, etc., dimethyl sulfoxide, dimethylformamide, etc., or a mixture thereof. The hydrolysis reaction can preferably be carried out at room temperature to 150° C., more preferably 50° to 110° C., for about 1 to about 6 hours.

The compound of this invention represented by the formula (I) can be isolated from products of partial hydrolysis of soyasaponin B (II) in which hydrolysis is conducted in water or a mixture of water and one or more of the above-described solvents in the presence of hydrogen halides such as hydrogen chloride, hydrogen bromide, etc., strong inorganic acids such as sulfuric acid, nitric acid, etc., or strong organic acids such as trichloroacetic acid, trifluoroacetic acid, etc. The term "partial hydrolysis" used herein means hydrolysis in which no splitting of the aglycone of the starting saponin B material occurs.

The isolation of the compound of this invention from the partial hydrolysate can be conducted using the above-described methods of isolation. For example, after extracting it with n-butanol to remove water-soluble components, the partial hydrolysate is subjected to silica gel column chromatography to separate it into respective components and the fraction corresponding to 3-O-(β-D-glucuronopyranosyl)-soyasapogenol B is subjected to crystallization from a suitable solvent, e.g., a mixture of chloroform and acetone (1:1 by volume). The partial hydrolysis can usually be performed at room temperature to 150° C., preferably 50° to 110° C., for about 1 to about 6 hours.

Alternatively, the compound represented by the formula (I) of this invention can be prepared utilizing microorganisms newly isolated by the present inventors.

The microorganism will be explained hereinbelow in greater detail.

I. PLACE OF OCCURRENCE

This strain was isolated from the soil at Tokushima City, Tokushima, Japan.

II. CHARACTERISTICS ON VARIOUS CULTURE MEDIA

The culture characteristics of this strain on various media based on visual and microscopic observations (FIG. 1) are as follows:

A. Visual Observation

(1) Malt Extract Agar Medium

The growth is rapid and irregular. The color of the back surface of the colony is tan (Tan, 3ie) to dark brown (Dk, Brown, 3pn). The colony is flat, and conidia formation is good. The color of the hyphae is biscuit (Biscuit, 2ec) to tan (Tan, 3ie) and liquid droplets which are exuded are observed. No soluble pigment is produced.

(2) Potato Glucose Medium

The growth is very rapid, and by cultivation at 27° C. for 30 days, the colony size reaches 70 mm. The peripheral part of the colony spreads dendritically, and adhered white hyphae are observed. A large number of liquid droplets are present. Hardly any spore formation is observed. The color of the back surface of the colony is light amber (Lt Amber, 3ie). No soluble pigment is formed.

(3) Czapek's Dox Agar Medium

The growth is poor.

(4) Synthetic Mucor Agar Medium

The growth in poor.

(5) Oatmeal Agar Medium

The growth is very good, so that in two weeks, the Petri dish is covered. The colony is thin and flat. Formation of hyphae is abundant from the initial stage of cultivation, and conidia formation is also rapid. The color of the colony changes from white to dark brown (Dk Brown, 3pn) as cultivation proceeds. Large quantities of liquid droplets occur on the hyphae. No soluble pigment is produced.

III. MORPHOLOGICAL PROPERTIES

The following can be seen from FIG. 1. The phialophores simply branch and stand erect. The phialophore tips slightly bulge in a rod form. However, the bulging is not so large as is observed in the type strains of Stachybotrys echinata IFO 7525 and 8856. This strain shows a hypha width of 4.0 to 4.5μ which is slightly larger than the phialophore. The phialophores which branch erect with foot cells from vegetative hyphae or aerial hyphae have two to three septa and have a size of 40–80×3.0–3.5μ. The cellular wall of the phialophore is not echinulate, but smooth.

Three to six phialide form from the bulged portion at the tips of the phialophores. Furthermore, spherical to sub-globose phialospores of one cell having an echinulate protrusion and a size of 4.3–5.2×3.0–4.2μ continuously form basipetally at the tips of the phialide and a chain of 24 to 70 conidia is formed. The phialide has an obclavate form, and has a size of 6.9–10.7×3.5–4.7μ.

The phialophores and phialide are colorless, and the phialide has a coffee (Coffee, 3pn) to black color.

The taxonomical status of the present strain having the above microbiological properties has been searched through G. L. Barron, *The Genera of Hyphomycetes from Soil,* The Williams & Wilkins Company, Baltimore (1968), J. C. Gilman, *A Manual of Soil Fungi,* The Iowa State University Press, Ames, Iowa (1971), and J. A. van Arx, *The Genera of Fungi Sporelating in Pure Culture,* Verag von J. Cremer 3301 Lehre (1970). According to the taxonomical system of Saccardo, the present strain belongs to Class Hyphomycetes, Family Dematiaceae, Genus Stachybotrys. In other words, the properties of the present strain characterized by the absence of ascocarps and other sexual reproductive organs, the formation of dark brown phialospores from phialide and the gathering of the resulting phialospores in a semicircular form at the top ends of the phialide agree well with the properties of the genus Stachybotrys.

The various characteristics of the present strain have been identified with reference to the above-described search manuals, and literature references such as G. R. Bisby, *Trans. Brit. Mycol. Soc.,* 26, 133–143 (1943), R. K. Zuck, *Mycologia,* 38, 69–76 (1946), G. L. Barron, *Can. J. Bot.,* 39, 153–157 (1961), and in comparison with the type strains preserved at the Institute for Fermentation, Osaka, Japan (IFO).

As a result, the present strain was found to belong to the genus Stachybotrys (genus Memmoniella). Specifically, the present strain does not possess ascocarps and other sexual reproductive organs, and dark brown phialospores form continuously from the phialide. Long chains of spores are formed. The properties of the present strain T-791 agree with those of the genus Stachybotrys (genus Memmoniella).

The various properties of the present strain have been searched through the aforesaid searching manuals and literature references such as R. K. Zuck, *Mycologia,* 38, 69–76 (1946) and G. Smith, *Trans. Brit. Mycol. Soc.,* 45, 387–394 (1962) and compared with the type strains preserved at IFO. As a result, it has been judged that since phialospores are formed continuously and basipetally from phialide, the strain T-791 belongs to *Memmoniella echinata* termed by Höhnel. However, from the reports of R. K. Zuck and G. Smith supra, the present strain T-791 was considered to be a strain analogous to *Stachybotrys echinata.* Hence, it was compared with *Stachybotrys echinata* IFO 7525 and IFO 8856.

Morphologically, echinulate protrusions specific to the two type strains are not observed on the cell walls of the phialophores in the present strain T-791. Furthermore, in the type strains, the tips of the phialophores bulge to 2 to 3 times the hypha width of the phialophores, however, no marked bulging is observed in the present strain. Furthermore, the two type strains show good growth on various culture media, especially on potato glucose agar medium, and form circular, somewhat raised colonies, and hyphae adhere abundantly. Furthermore, conspicuous conidia formation is observed. In contrast, the present strain shows a dendritic irregular growth as stated hereinabove, and poor hypha formation and poor conidia formation are observed. From the above microbiological differences, the present strain has been considered to be a new strain, and named Stachybotrys sp. T-791.

The indication of the colors above and hereinafter is in accordance with the method described in *Color Har-*

*mony Manual,* Container Corporation of America (1958).

IV. PHYSIOLOGICAL PROPERTIES

Stachybotrys sp. T-791 is an aerobic strain, and has the following physiological properties.

| Stachybotrys sp. T-791 | pH | Temperature |
| --- | --- | --- |
| Growth Conditions: | 3.5–11.5 | 15°–38° C. |
| Optimal Growth Conditions: | 4.5– 9.5 | 20°–30° C. |

Samples of the new strain, Stachybotrys sp. T-791 have been deposited at the Fermentation Research Institute, Agency of Industrial Science and Technology, Japan (at No. 8-1, Inage Higashi 5-chrome, Chiba-shi, Chiba, Japan) under deposit number FERM-P No. 3803 and also deposited at the American Type Culture Collection (12301 Parklawn Drive Rockville, Md., U.S.A. 20852) under deposit number ATCC 20513.

Specifically, the preparation of the compound of this invention by the microorganism of the genus Stachybotrys described above is achieved in the following manner.

The microorganisms are first cultivated in a medium containing ordinary nutrient sources and additives. Nitrogen sources generally used as a cultivating substrate include, for example, soybean powder, soybean oil, corn steep liquor, yeast extract, dried yeast, oatmeal, meat extract, hydrolyzed casein, ammonium salts, and nitrate salts. Examples of suitable carbon sources are glucose, glycerol, maltose, starch, lactose, sucrose, and molasses. Examples of additives to the culture medium include inorganic salts such as calcium carbonate, sodium chloride, magnesium sulfate, and phosphoric acid. If required, the culture medium may further contain tiny amounts of salts of metals such as iron, copper, manganese, and zinc. Cultivation can be performed in an ordinary aqueous medium containing the above substrate using a surface cultivating technique or a submerged cultivation technique with aeration and stirring. Submerged cultivation with aeration and stirring is preferred. The cultivation can be advantageously carried out at a temperature of 15° to 38° C., preferably 20 to 32° C., for a period of usually 3 to 7 days under ordinary aeration conditions while maintaining the pH of the culture medium at 3.5 to 11.5, preferably 4.5 to 9.5.

After the cultivation, the substance produced is recovered from the culture broth. The method of recovery is not particularly restricted, and various known methods utilizing the physicochemical properties of the substances produced can be employed. Recovery can be accomplished, for example, by a method utilizing the differences in solubility between the products and impurities, a method utilizing the differences in adsorptive power and affinity for ordinary adsorbents such as activated carbon, XAD-2, silica gel, ion exchange resins, Sephadex, etc., a method utilizing the differences in the coefficient of distribution between two liquid phases, and a combination of such methods.

The compound of this invention thus prepared can form salts with various pharmaceutically acceptable basic compounds. Of course, this invention includes within the scope thereof such salts.

Suitable examples of the basic compounds which can be used for forming the above salts include inorganic basic compounds, for example, sodium hydroxide, potassium hydroxide, aluminum hydroxide, sodium carbonate, potassium carbonate, sodium hydrogen carbonate, etc., and organic basic compounds, for example, piperazine, morpholine, piperidine, ethylamine, dimethylamine, triethylamine, etc.

The compounds of this invention can be used as a nephritis treating agent, and when used for this purpose are formulated into pharmaceutical compositions together with ordinary pharmaceutically acceptable carriers. Suitable carriers which can be used are, for example, diluents or excipients such as fillers, extenders, binders, wetting agents, disintegrants, surface active agents and lubricants which are usually employed to prepare such drugs depending on the dosage form.

Various dosage forms of the therapeutic agents as a nephritis treating agent can be selected according to the purpose of the therapy. Typical dosage forms which can be used are tablets, pills, powders, liquid preparations, suspensions, emulsions, granules, capsules, suppositories, and injectable preparations (solutions, emulsions, suspensions, etc.).

In molding a pharmaceutical composition containing the compounds of this invention as an active ingredient into a tablet form a wide range of carriers known in the art can be used. Examples of suitable carriers include excipients such as lactose, white sugar, sodium chloride, glucose, urea, starch, calcium carbonate, kaolin, crystalline cellulose and silicic acid; binders such as water, ethanol, propanol, simple syrup, glucose, starch solution, gelatin solution, carboxymethyl cellulose, shellac, methyl cellulose, potassium phosphate and polyvinyl pyrrolidone; disintegrants such as dried starch, sodium alginate, agar powder, laminaria powder, sodium hydrogen carbonate, calcium carbonate, Tween, sodium lauryl sulfate, stearic acid monoglyceride, starch, and lactose; disintegration inhibitors such as white sugar, stearic acid glyceryl ester, cacao butter and hydrogenated oils; absorption promoters such as quaternary ammonium bases and sodium lauryl sulfate; humectants such as glycerol and starch; adsorbents such as starch, lactose, kaolin, bentonite and colloidal silicic acid; and lubricants such as purified talc, stearic acid salts, boric acid powder, Macrogol and solid polyethylene glycol.

In molding the pharmaceutical composition into a pill form, a wide variety of conventional carriers known in the art can be used. Examples of suitable carriers are excipients such as glucose, lactose, starch, cacao butter, hardened vegetable oil, kaolin and talc, binders such as gum arabic powder, tragacanth powder, gelatin, and ethanol, and disintegrants such as laminaria and agar. The tablets, if desired, can be coated, and made into sugar-coated tablets, gelatin-coated tablets, enteric-coated tablets, film-coated tablets, or tablets coated with two or more layers.

In molding the pharmaceutical composition into a suppository form, a wide variety of carriers known in the art can be used. Examples of suitable carriers include polyethylene glycol, cacao butter, higher alcohols, esters of higher alcohols, gelatin, and semi-synthetic glycerides.

When the pharmaceutical composition is formulated into an injectable preparation, the resulting solution and suspension are preferably sterilized, and are isotonic with respect to the blood. In formulating the pharmaceutical composition into the form of a solution or suspension, all diluents customarily used in the art can be used. Examples of suitable diluents are water, ethyl alcohol, propylene glycol, ethoxylated isostearyl alcohol, polyoxyethylene sorbitol, and sorbitan esters. Sodium chloride, glucose or glycerol may be incorporated into a therapeutic agent, e.g., as a nephritis treating agent in an amount sufficient to prepare isotonic solutions. The therapeutic agent may further contain ordinary dissolving aids, buffers, pain-alleviating agents, and preservatives, and optionally coloring agents, perfumes, flavors, sweeteners, and other drugs.

The amount of the compound of this invention as an active ingredient to be incorporated into a pharmaceutical composition useful as a nephritis treating agent is not particularly limited, and can vary over a wide range. A suitable therapeutically effective amount of the compound of this invention is usually 1 to 70% by weight, preferably 5 to 50% by weight, based on the entire composition.

There is no particular restriction on the manner of using the therapeutic agent as an anticomplementary agent such as a nephritis treating agent, and the therapeutic agent can be administered by routes suitable for the particular forms of the therapeutic agent. For example, the tablets, pills, liquid preparations, suspensions, emulsions, granules, and capsules are orally administered. The injectable preparations are intravenously administered either alone or together with ordinary auxiliary agents such as glucose and amino acids. Furthermore, as required, the therapeutic agent can be administered intramuscularly, intracutaneously, subcutaneously, or intraperitoneally. The suppository is administered intrarectally.

The dosage of the nephritis treating agent is suitably selected according to the purpose of use, the symptoms, etc. Usually, a dosage of the compound of this invention is about 0.5 to 20 mg/kg of body weight per day.

The compounds of this invention have anticomplementary activities, and are useful also as therapeutic agents for autoimmune diseases, collagen diseases, and rheumatic diseases.

The results of tests on the pharmacological effects of the compounds of this invention are shown below.

PHARAMACOLOGICAL TESTING

1. Compounds Tested

A. 3-O-($\beta$-D-glucuronopyranosyl)-soyasapogenol B (Invention)

B. Glycyrrhizin (Comparison)

2. Anticomplementary Activity

The anticomplementary activity of the test compounds above was measured and confirmed by the testing method described in Meneki Kagaku (Immuno-Chemistry), Yuichi Yamamura et al., Ed. Asakura Shoten, Tokyo, Japan (1973) pages 830–834. Specifically, a test tube was charged with 0.5 ml of an aqueous dispersion of each of the test compounds, 0.5 ml of sensitized erythrocytes (EA) containing $1 \times 10^8$ cells/ml, 1 ml of a 5-fold diluted solution of a Veronal buffer solution containing isotonic gelatin (This 5-fold diluted solution is termed GVB++ for brevity), and 0.5 ml of complement serum (guinea pig complement) diluted 150 times with the GVB++. The mixture was maintained for 60 minutes. Then, 5 ml of an ice-fold physiological saline solution was added thereto and the mixture was centrifuged. The absorbance of the supernatant separated was measured at $OD_{413}$, and the extent the test compound inhibited the hemolysis of the sensitized erythrocytes was determined. The 50% hemolysis inhibitory activity value ($\gamma$/ml) measured by the above method is shown in Table 1 below for each test compound.

3. Acute Toxicity

The actute toxicity ($LD_{50}$ mg/kg) of the test compounds was determined on mice by intraperitoneal administration in the case of Compound A and intravenous administration in the case of Compound B.

The results obtained are shown in Table 1 below.

TABLE 1

| Test Compound | Anticomplementary Activity ($\gamma$/ml) | Acute Toxicity $LD_{50}$ (mg/kg) |
|---|---|---|
| A | 5 | Above 300 |
| B | 500–1,000 | Above 300 |

As will be clear from the results shown in Table 1 the acute toxicity ($LD_{50}$) value of the compound of this invention is of an order enabling one to use it as a therapeutic agent.

4. Therapeutic Effect on Nephrotoxin-Type Nephritis

Rat nephrotoxin ("NT" for brevity) was obtained as described below.

Rat kidney cortex was homogenized with an equal quantity of physiological saline. The homogenized mixture was mixed with Freund's complete adjuvant (a product of Difco Company) in a volume ratio of 1:1. 2 ml of the resulting mixture was intramuscularly injected into a rabbit (body weight 3,100 g) to immunize the rabbit. A month and a half later, blood was taken from the heart of the rabbit and serum was obtained. The resulting serum was inactivated at 56° C. for 30 minutes, then salted out with a 40% saturated aqueous solution of ammonium sulfate, and fractionated. The $\gamma$-globulin (IgG) fraction was collected to obtain NT.

The therapeutic evaluation was carried out using male Wistar rats with a body weight of 150 to 160 g with three replications for each test compound. The test compound was intraperitoneally administered once every 24 hours for seven days. One hour after the administration of the test compound on the third day, the NT was applied. The NT was intravenously injected in an amount of 1 ml at a tail vein of each rat. Physiological saline solution was used as a control.

The proteinuria level (total amount excreted into the urine over a 24 hour period) was measured using turbidometry employing bovine serum albumin as a control by means of sulfosalicylic acid.

The results obtained are shown in Table 2 below.

TABLE 2

| | Proteinuria Level (mg/day) | | | |
|---|---|---|---|---|
| | | Day Number | | |
| | 1 | 4 | 7 | 10 |
| Control 1 | 14 | 17 | 22 | 32 |
| 2 | 20 | 25 | 27 | 37 |
| 3 | 12 | 19 | 20 | 31 |
| Average | 15 | 20 | 23 | 33 |
| Compound of Invention (3 mg/body) 1 | 1.9 | 1.2 | 0.9 | 7 |
| 2 | 5.3 | 2.9 | 1.8 | 13 |
| 3 | 2.5 | 2.7 | 1.1 | 9 |
| Average | 3.2 | 2.3 | 1.3 | 9.7 |

The day number above is counted from the time of administration of the test compound which was 1 hour before the application of the NT.

The proteinuria level in a healthy rat is 0.5 to 5 mg/day. When the proteinuria level exceeds this range, especially when the proteinuria level is more than 10 mg/day, it may safely be said that nephritis has occurred. As can be seen from the results in Table 2, nephritis occurred in the control lot, and in the case of the compounds of the present invention, the amount of proteinuria from the time of administration of NT to 10 days after administration is substantially the same as that of a healthy rat. Thus, the administration of the compounds of this invention can be seen to inhibit primary and secondary immune reactions.

5. Therapeutic Effects on Heymann-Type Nephritis

Male Wistar rats with a body weight of 180 to 200 g were used in the test. Rat kidney cortex was extracted, and homogenized with an equal quantity by volume of a physiological saline solution. The homogenate was centrifuged at 1,500 G for 1 hour. The supernatant liquid was purified in accordance with the method of T. S. Edgington et al., *Journal of Experimental Medicine*, 127, 555 (1968), and mixed with Freund's complete adjuvant 37 Ra (a product of Difco Company) in a volume ratio of 0.4:1. The resulting mixture was injected intraperitoneally into isologous rats in an amount of 0.5 ml per rat. And then the same amount of its mixture was administered every 2 weeks until the proteinuria level exceeded 100 mg/day. (This period was about 6 to 8 weeks.)

Each of the test compounds was intraperitoneally administered to the rats affected with Heymann-type nephritis (with a body weight of 300 to 350 g) once a day for 7 days, and then the amount of proteinuria (mg/day) was measured in the same manner as described above. Physiological saline solution was used as a control. The results obtained are shown in Table 3 below.

TABLE 3

| | | Proteinuria Level (mg/day) | | | | | |
|---|---|---|---|---|---|---|---|
| | | Before Administration | Day Number | | | | |
| | | | 1 | 4 | 7 | 14 | 21 |
| Control | 1 | 132 | 127 | 135 | 126 | 135 | 114 |
| | 2 | 121 | 105 | 121 | 109 | 103 | 105 |
| | 3 | 135 | 117 | 137 | 132 | 121 | 109 |
| | Average | 129 | 116 | 131 | 122 | 119 | 109 |
| Compound of Invention (3 mg/body) | 1 | 117 | 89 | 42 | 27 | 3 | 8 |
| | 2 | 129 | 127 | 75 | 39 | 17 | 13 |
| | 3 | 123 | 119 | 58 | 18 | 9 | 7 |
| | Average | 123 | 112 | 58 | 28 | 3 | 9 |

Two to three weeks after the beginning of the testing, the body weights of the rats increased to 400 to 500 g, and normal proteinuria levels are believed to be 5 to 15 mg/day. As can be seen from the results in Table 3, the compounds of the present invention can cure Heymann-type nephritis.

To illustrate the present invention in more detail, the production of the compounds of this invention represented by the general formula (I) and the salts thereof are described in the following Examples, and the production of nephritis treating agents containing the compounds of the invention of the general formula (I) and the salts thereof as an active ingredient are described in the following Reference Examples.

EXAMPLE 1

(a) Soyasaponin B (500 mg) was dissolved in 30 ml of methanol. After adding 1.5 ml of a 15 N sulfuric acid, the solution was refluxed for 3.5 hours. Cold water was added to the reaction mixture to form precipitates which were collected and washed with water sufficiently. The precipitates were adsorbed on a silica gel column and developed with a mixture of chloroform-ethanol in turn (20:1 by volume 200 ml; 10:1 by volume 150 ml; 5:1 by volume 200 ml; and 2:1 by volume 200 ml) to obtain 71 mg of 3-O-(6-O-methyl-$\beta$-D-glucuronopyranosyl)-soyasapogenol B.

The compound thus-obtained was dissolved in 2 ml of methanol and 2 ml of a 1 N aqueous NaOH solution was added to the solution, followed by refluxing for 2 hours. After the reaction mixture was mixed with cold water and the pH value adjusted to about 1 with a 1 N aqueous HCl solution, it was extracted with n-butanol. The n-butanol fraction was concentrated to dryness under reduced pressure. Crystallization of the residue from a mixture of chloroform-acetone (1:1 by volume) afforded 50 mg of 3-O-($\beta$-D-glucuronopyranosyl)-soyasapogenol B.

Melting Point: 231°–232° C. (decomposition)

| Elemental Analysis for $C_{36}H_{58}O_9$: | | |
|---|---|---|
| | C | H |
| Calculated (%): | 68.11 | 9.21 |
| Found (%): | 67.85 | 9.08 |

Silica Gel Thin Layer Chromatography Using "Kiesel Gel $F_{254}$" (a trade name for a product of Merck Co.)
1. Chloroform-Methanol-Water (65:35:8 by volume) $R_f=0.38$
2. Isopropanol-2 N Aqueous Ammonia Solution (100:15 by volume) $R_f=0.21$ Solubility: Very soluble in methanol, ethanol, n-propanol, n-butanol, aqueous alkali solution, pyridine, dimethyl sulfoxide and dimethylformamide; soluble in acetone, ethyl acetate and methyl ethyl ketone; and sparingly soluble in benzene, chloroform, diethyl eter, n-hexane and petroleum ether.

(b) Soyasaponin B (500 mg) was dissolved in 30 ml of ethanol saturated with hydrogen chloride and the solution was refluxed for 3 hours. Cold water was added to the reaction mixture to form precipitates which were collected and washed with water. The precipitates were then purified through a silica gel column chromatography (eluant: chloroform-ethanol (20:1, 10:1, 5:1 and 2:1 by volume)) to obtain 75 mg of 3-O-(6-O-ethyl-$\beta$-D-glucuronopyranosyl)-soyasapogenol B.

The compound thus-obtained was mixed with 2 ml of ethanol and 2 ml of a 1 N aqueous KOH solution and the mixture was refluxed for 2 hours. The reaction mixture was mixed with cold water and the pH value adjusted to about 1 with a 1 N aqueous HCl solution followed by extraction with n-butanol. The n-butanol fraction was concentrated to dryness under reduced pressure and crystallization of the residue from a mixture of chloroform-acetone (1:1 by volume) afforded 45 mg of 3-O-($\beta$-D-glucuronopyranosyl)-soyasapogenol B.

Melting Point: 231°–232° C. (decomposition)

EXAMPLE 2

Soyasaponin B (1 g) was dissolved in 70 ml of distilled water and the solution was mixed with 5 ml of a 15

N aqueous sulfuric acid solution followed by refluxing for 2.5 hours. The reaction mixture was extracted with n-butanol. The n-butanol fraction was concentrated to dryness under reduced pressure. The residue was adsorbed on a silica gel column and developed with a mixture of chloroform-ethanol (20:1, 10:1, 5:1 and 2:1 by volume) to obtain 350 mg 3-O-($\beta$-D-glucuronopyranosyl)-soyasapogenol B.

Melting Point: 231°–232° C. (decomposition)

EXAMPLE 3

A 500 ml Sakaguchi flask was charged with 100 ml of a culture medium of the following formulation, and Stachybotrys sp. T-791 was cultivated at 25° C. and a pH of 5.5 for 4 days with shaking.

Glycerol: 0.5%
Starch: 1.0%
Sucrose: 0.2%
Soybean Powder: 0.5%
Peptone: 0.1%
Malt Extract: 0.2%
$MgSO_4$: 0.3%
HCl: 0.05%

A 30-liter jar fermentor was charged with 20 liters of a culture medium of the above formulation, and one flask of the resulting seed culture was cultivated in the culture medium at 28° C. for 5 days with stirring at 300 rpm at an aeration rate of 1 liter per liter of the culture medium per minute. The resulting culture broth was centrifuged at a speed of 8,000 rpm to remove the microbial cells and the pH value of the supernatant liquid was adjusted to about 1 with concentrated hydrochloric acid. The resulting precipitates were collected by centrifugation and extracted with methanol. The methanol fraction was adsorbed on a column of activated carbon (500 ml) after it was concentrated under reduced pressure. The column was eluted with an aqueous 30% acetone solution and then with an aqueous 50% acetone solution. The fraction of aqueous 50% acetone solution was collected and concentrated to dryness under reduced pressure. The residue was adsorbed on a silica gel column and developed using a mixture of chloroform and acetone (2:1 and 1:1 by volume) as an eluant. On the other hand, a fraction containing 3-O-($\beta$-D-glucuronopyranosyl)-soyasapogenol B (corresponding to the fraction having $R_f$ value of 0.38 which was obtained by subjecting "Kiesel Gel $F_{254}$" (a trade name for a product of Merck Co.) to a thin layer chromatography using a mixture of chloroform-methanol-water (65:35:8 by volume) as a developing solution) was collected and concentrated to dryness under reduced pressure. The concentrate was again adsorbed on a silica gel column and developed with a mixture of chloroform-acetone in turn (2:1 and 1:1 by volume) and the fraction corresponding to the above-described one was collected followed by concentrating to dryness. Crystallization of the residue from a mixture of chloroform-acetone (1:1 by volume) afforded 46 mg of 3-O-($\beta$-D-glucuronopyranosyl)-soyasapogenol B.

Melting Point: 231°–232° C. (decomposition)

REFERENCE EXAMPLE 1

Sodium Salt of the Compound of the Invention: 500 mg
Glucose: 250 mg
Distilled Water for Injection: to make the total amount 5 ml The sodium salt and glucose were dissolved in distilled water for injection, and the solution was poured into a 5 ml ampoule. The air was purged with nitrogen, and the ampoule was heated at 121° C. for 15 minutes to sterilize the solution to obtain an injectable preparation.

REFERENCE EXAMPLE 2

Compound of the Invention: 750 mg
Semi-synthetic Glyceride Base: to make the total amount 2,000 mg Compound of the invention was added to the semi-synthetic glyceride base, and they were mixed and suspended at 50° C. The mixture was cast into a mold, and allowed to cool naturally. The product was removed, and thus, a suppository was obtained.

REFERENCE EXAMPLE 3

Compound of the Invention: 150 g
Avicel (trademark for a product of Asahi Kasei Kabushiki Kaisha): 40 g
Corn Starch: 30 g
Magnesium Stearate: 2 g
TC-5 (trademark for hydroxypropylmethyl cellulose): 10 g
Polyethylene Glycol: 3 g
Castor Oil: 40 g
Methanol: 40 g The compound of this invention, the Avicel, the corn starch and the magnesium stearate were mixed and ground, and then tableted using a conventional pounder (R 10 mm) for sugar coating. The resulting tablets were coated with a film coating agent composed of TC-5, polyethylene glycol 6000, castor oil and methanol to produce film-coated tablets.

While the invention has been described in detail and with reference to specific embodiments thereof, it will be apparent to one skilled in the art that various changes and modifications can be made therein without departing from the spirit and scope thereof.

What is claimed is:

1. 3-O-($\beta$-D-glucuronopyranosyl)-soyasapogenol B represented by the formula (I):

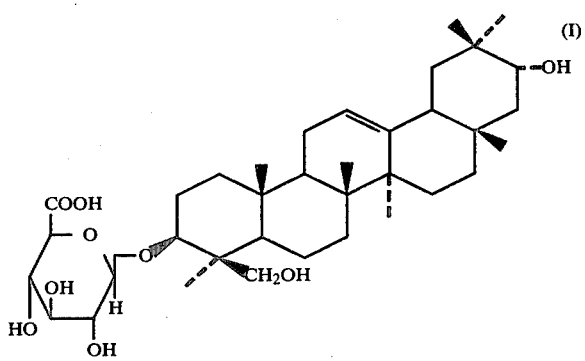

and pharmaceutically acceptable salts thereof.

2. A pharmaceutical composition having anticomplementary activity in animals comprising a therapeutically effective amount of the soyasapogenol derivative of the formula (I) or a pharmaceutically acceptable salt thereof

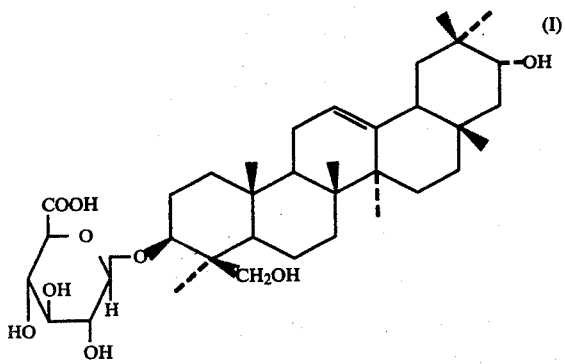

and a pharmaceutically acceptable carrier.

3. The composition according to claim 2, wherein the amount of the soyasaponin derivative or the pharmaceutically acceptable salt thereof is about 1 to 70% by weight based on the entire weight of the pharmaceutical composition.

4. An antinephritic pharmaceutical composition comprising a therapeutically effective amount of the soyasapogenol derivative of the formula (I)

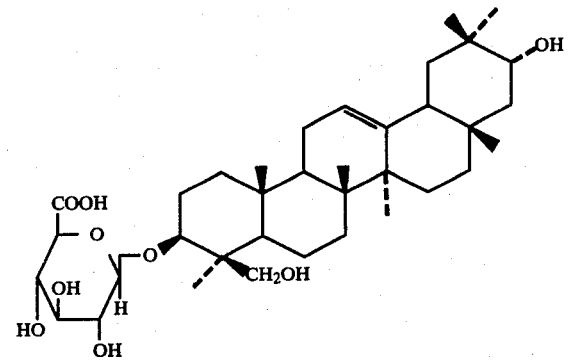

or a pharmaceutically acceptable salt thereof and a pharmaceutically acceptable carrier.

5. A method for treating nephritis, which comprises administering the composition according to claim 4 to a nephritic patient in a daily dose of about 0.5 to about 20 mg/kg of body weight.

* * * * *